(12) United States Patent
Touitou

(10) Patent No.: US 9,668,987 B2
(45) Date of Patent: Jun. 6, 2017

(54) COMPOSITIONS FOR NAIL AND SKIN TREATMENT

(75) Inventor: Elka Touitou, Jerusalem (IL)

(73) Assignee: YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 41 days.

(21) Appl. No.: 13/137,259

(22) Filed: Aug. 1, 2011

(65) Prior Publication Data

US 2012/0114574 A1 May 10, 2012

Related U.S. Application Data

(63) Continuation-in-part of application No. PCT/IB2010/000170, filed on Jan. 29, 2010, and a continuation-in-part of application No. PCT/IB2010/000171, filed on Jan. 29, 2010.

(60) Provisional application No. 61/148,799, filed on Jan. 30, 2009.

(51) Int. Cl.

| | | |
|---|---|---|
| A61K 31/37 | (2006.01) |
| A61K 31/5375 | (2006.01) |
| A61K 31/343 | (2006.01) |
| A61K 31/496 | (2006.01) |
| A61K 31/4174 | (2006.01) |
| A61P 17/12 | (2006.01) |
| A61K 33/22 | (2006.01) |
| A61K 31/045 | (2006.01) |
| A61P 31/10 | (2006.01) |
| A61P 17/00 | (2006.01) |
| A61P 31/12 | (2006.01) |
| A61P 29/00 | (2006.01) |
| A61K 31/137 | (2006.01) |
| A61K 9/00 | (2006.01) |
| A61K 9/127 | (2006.01) |
| A61K 9/70 | (2006.01) |
| A61K 31/4418 | (2006.01) |
| A61K 31/192 | (2006.01) |

(52) U.S. Cl.
CPC .......... *A61K 31/137* (2013.01); *A61K 9/0014* (2013.01); *A61K 9/127* (2013.01); *A61K 9/70* (2013.01); *A61K 9/7015* (2013.01)

(58) Field of Classification Search
None
See application file for complete search history.

(56) References Cited

U.S. PATENT DOCUMENTS

| | | | |
|---|---|---|---|
| 4,615,699 A | 10/1986 | Gale et al. | |
| 4,681,584 A | 7/1987 | Gale et al. | |
| 5,716,638 A | 2/1998 | Touitou | |
| 6,231,875 B1 | 5/2001 | Sun et al. | |
| 6,585,963 B1 * | 7/2003 | Quan et al. | 424/61 |
| 6,846,837 B2 | 1/2005 | Maibach et al. | |
| 2003/0091519 A1* | 5/2003 | Zatz et al. | 424/61 |
| 2003/0235541 A1 | 12/2003 | Maibach et al. | |
| 2008/0107735 A1 | 5/2008 | Gyurik et al. | |
| 2008/0188568 A1 | 8/2008 | Suvanprakorn et al. | |

FOREIGN PATENT DOCUMENTS

| | | |
|---|---|---|
| EP | 0 253 619 | 1/1988 |
| WO | 99/49835 | 10/1999 |
| WO | 2004/084826 | 10/2004 |
| WO | 2008/121709 | 10/2008 |
| WO | 2009/127825 | 10/2009 |

OTHER PUBLICATIONS

Berner et al. (Journal of Pharmaceutical Sciences vol. 78, No. 5, May 1989).*
Gupta et al., "Antifungal Agents: An Overview, Part I," Journal of the American Academy of Dermatology, C.V. Mosby, St. Louis, Mo. vol. 30, No. 5, May 1, 1994, pp. 677-698.
Supplementary European Search Report issued for European Patent Application No. EP 10 73 5528 dated Aug. 6, 2012 (2 pages).
Supplementary European Search Report issued for European Patent Application No. EP 10 73 5529 dated Jun. 29, 2012 (1 page).
International Search Report for PCT/IB2010/000170, mailed Jun. 17, 2010.
International Search Report for PCT/IB2010/000171, mailed Jun. 17, 2010.
Reichek et al., "Antianginal Effects of Nitroglycerin Patches" Am. J. Cardiology, 54(1):1-7(1984).
Elkayam et al., "Hemodynamic and Hormonal Effects of High-Dose Transdermal Nitroglycerin in Patients with Chronic Congestive Heart Failure" Am. J. Cardiol 56:555-559 (1985).
Rajfer, et al., "Sustained Beneficial Hemodynamic Responses to Large Doses of Transdermal Nitroglycerin in Congestive Heart Failure and Comparison with Intravenous Nitroglycerin" Am. J. Cardiol. 54:120-125 (1984).

* cited by examiner

*Primary Examiner* — Patricia Duffy
*Assistant Examiner* — Garen Gotfredson
(74) *Attorney, Agent, or Firm* — Browdy and Neimark, PLLC

(57) ABSTRACT

Novel topical compositions for the treatment of nail and skin afflictions comprising at least one active agent, at least one volatile solvent, at least one film-forming ingredient and at least one phospholipid, processes for their preparation and methods of treatment of nail and skin afflictions. Following application of the compositions and evaporation of volatile solvents, the composition produces a film, which has web-like structures containing the active agent(s).

30 Claims, 17 Drawing Sheets

COMPOSITIONS FOR NAIL AND SKIN TREATMENT

BACKGROUND OF THE INVENTION

Nail fungal infections are a widespread and hard to cure affliction, and so are some other skin afflictions. While several systemic and topical treatments are commercially available, none is completely satisfactory, as evidenced by the continuous effort to find new therapeutic methods. The nail fungal infection known as onychomycosis, caused mainly by the dermatophyte trichphyton rubrum, is particularly difficult to treat, and while some treatments prove effective, there are significant side-effects and the infection is recurrent.

The most prominent drugs for nail fungal infections are terbinafine and ciclopirox. Other antifungal drugs in use or development include griseofulvin, posaconazole, amorolfine, itraconazole, econazole and butenafine.

Terbinafine (Lamisil®), a very effective drug for the treatment of onychomycosis (tinea unguium), is mainly administered systemically, despite the known side-effects like liver toxicity. Terbinafine is commercially available also as the 1% Lamisil® OTC topical cream, but the indications for the cream are different.

The significant side-effects are the main reason why topical treatments, likely to diminish the systemic effects, are being coveted, and attempts are being made to develop efficient topical drugs, with minimal side-effects.

The FDA www.ClinicalTrials.gov site lists 15 clinical studies with terbinafine, mostly topical treatments against onychomycosis, including terbinafine nail lacquer. Higher concentrations of terbinafine and alternative actives, like posaconazole and 5% amorolfine nail lacquer are being investigated as possible treatment for nail fungal infections, which evidences the fact that there is still an unmet medical need for safe and effective topical treatments of nail fungal infections. Only four clinical studies are listed on this site for ciclopirox, out of which none for onychomycosis or other nail infections, which shows that ciclopirox is not considered a preferred treatment, while terbinafine is.

Another antifungal drug, ciclopirox, of limited antifungal activity, is administered only topically. The commercial product Penlac® nail lacquer is a 8% ciclopirox topical solution which is applied once daily and repeatedly to the nail and to the skin beneath it to form a lacquer layer. Another commercial nail lacquer is 5% amorolfine, commercially available as OTC in the UK as Loceryl or Curanail.

The nail application of Penlac® results in formation of a dry film, after evaporation of the liquid components of the composition. Penlac® composition includes the following ingredients: each gram of PENLAC® NAIL LACQUER (ciclopirox) Topical Solution, 8%, contains 80 mg ciclopirox in a solution base consisting of ethyl acetate, NF; isopropyl alcohol, USP; and butyl monoester of poly[methylvinyl ether/maleic acid] in isopropyl alcohol. Ethyl acetate and isopropyl alcohol are solvents that vaporize after application.

The activity of the topical lacquers like Penlac® depends in large measure on the composition of the film that forms on the nail after the evaporation of the solvents. In the Penlac® case, after the evaporation of the solvents, the film is formed by ciclopirox in butyl monoester of poly[methylvinyl ether/maleic acid (Gantrez® ES-435), a copolymer.

Conventional antifungal compositions, however, exhibit poor to marginal efficacy against nail fungal infections, and there is clearly an unmet need for antifungal compositions with improved efficacy in the treatment of nail fungal infections.

SUMMARY OF THE INVENTION

The present invention successfully addresses unmet medical needs, providing innovative drug delivery systems that result in structured films having as main elements the active agent(s), phospholipids and a film-forming ingredient.

The compositions of the present invention are liquid compositions comprising at least one active agent, at least one volatile solvent, at least one film-forming ingredient, at least one phospholipid and, optionally, other pharmaceutically acceptable ingredients. In one preferred embodiment, the active agent is terbinafine and/or one or more terbinafine salts, and hence the compositions of the present invention in this case are liquid compositions comprising terbinafine and/or one or more terbinafine salts, at least 61% (w/w) of at least one volatile solvent, at least one film-forming ingredient, at least one phospholipid and, optionally, other pharmaceutically acceptable ingredients.

In another preferred embodiment, the active agent is Ibuprofen. Preferably, in this case the composition comprises from 0.3 to 15% w/w Ibuprofen.

The compositions of the invention preferably are applied to the nail or skin treated surfaces as solutions that are in the form of a lacquer. After the compositions of the invention are applied, rapid drying of the volatiles results in a film on the treated surface, which film exhibits a web-like structure containing the active agent(s), the phospholipid(s), and, optionally other pharmaceutically acceptable ingredients, which may include residual solvents. These structured arrangements exhibit sustained and improved delivery of the active agent to the treated nail or skin. While not wishing to be bound by any specific theory, it is believed that the improved delivery is due to the reservoir effect of the web-like structures.

The film formed adheres to the skin or nail surface, is substantive to it, and contains the drug incorporated mainly in the web-structure which probably acts as a reservoir for the active agent. The compositions of this invention contain a sufficiently high concentration of volatile solvent(s) to afford a rapid formation of a continuous, cohesive film on the treated nail or skin surface. The structures in the film are formed due to the presence of phospholipids and film-forming ingredient in the composition. In the absence of phospholipids, no such web-like structure as are observed. The presence of volatile solvents in the composition allows for quick formation of stable and continuous films.

After rapid evaporation of the solvents, a thin and continuous film containing structures resembling a web is formed on the treated surface.

Microscopy study of the films obtained from the compositions of the present invention show that a unique structure is formed and maintained in the film. Fluorescence Microscopy (FIG. 1) shows web-like arrangement structures dispersed throughout the film.

This system allows for improved and sustained drug delivery and drug retention into the tissue, which is believed to be due to the reservoir effect and the phospholipid's presence and effect.

The composition may be applied once to multiple times per day and repeated until complete remission. The effectiveness of the compositions of the present invention enables a shortened period of treatment with superior results.

These and other aspects of the invention will become apparent from the description of the invention, which follows.

DETAILED DESCRIPTION OF THE INVENTION

Figure 1:
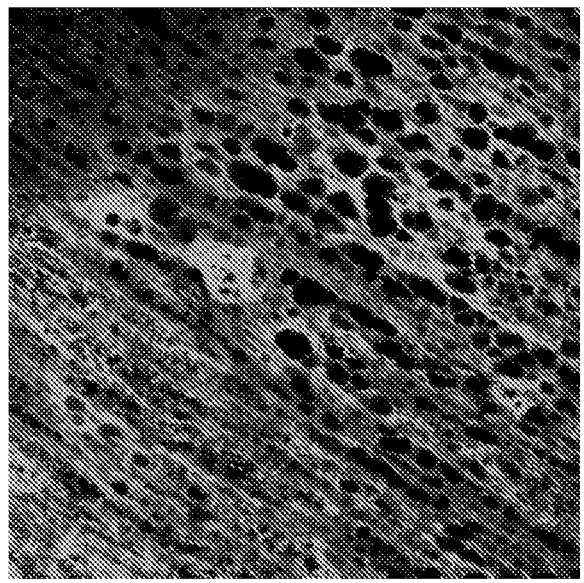
FIG. 1 depicts a fluorescence micrograph image of film obtained from Formulation No. I-Olympus Fluoview 1XLO Confocal Laser Scanning Microscope. The probe used—Fluorescein DHPE (N-(fluorescein-5-thiocarbamoyl)-1,2-dihexadecanoyl-sn-glycero-3-phosphoethanolamine, triethylammonium salt) Invitrogen™. The web structure incorporating the probe is evident in the micrograph.

This invention provides compositions for topical application, resulting in structured continuous, cohesive films following rapid evaporation of the volatiles in the composition, said films containing web-like structures serving as drug reservoirs.

The present invention also provides liquid compositions, that can be applied on the nail or skin, to form a structured webbed film after application.

The present invention additionally provides liquid compositions, that can be applied on the nail or skin for medical use, cosmetic use or veterinary use.

It has been surprisingly found that compositions comprising a phospholipid, a film-forming ingredient and high concentration of volatile solvents (for example, at least 50% (w/w)), result in films exhibiting novel and hitherto unknown web-like structures. When the compositions comprise one or more active agents, these active agents become part of the web, which is acting like a reservoir for the active agent(s).

In an embodiment of this invention, there are provided compositions comprising an active agent, a phospholipid, at least one volatile solvent, optionally water and/or a glycol and at least one film-forming ingredient, wherein a cohesive film exhibiting a web-like structure is formed on application on the treated nail or skin and rapid subsequent evaporation of the volatiles.

Preferably, the at least one active agent is selected from ciclopirox, amorolfine, griseofulvine, posaconazole, itraconazole, econazole, ibuprofen, butenafine, borax, geraniol, terbinafine and salts thereof, and combinations thereof.

The film-forming ingredient, the phospholipid, other ingredients, residual solvent(s) and the active are part of the novel webbed structures.

In one preferred embodiment of this invention, there are provided compositions comprising terbinafine or a salt thereof as the active agent, a phospholipid, at least one volatile solvent, optionally water and/or a glycol and at least one film-forming ingredient, wherein a cohesive film exhibiting a web-like structure is formed on application on the treated nail or skin and rapid subsequent evaporation of the volatiles.

In another preferred embodiment, the active agent is Ibuprofen. Preferably, in this case the composition comprises from 0.3 to 15% w/w Ibuprofen.

The compositions of this invention are preferably liquid, in the form of solution, lotion, low viscosity gel, spray, lacquer, foam, emulsion, patch, drug reservoir, suspension or cream.

The compositions of the present invention comprise a therapeutically effective amount of drug or agent (e.g., an antifungal agent or terbinafine and/or one or more terbinafine salts), and pharmaceutically/cosmetically acceptable inactive ingredients.

The agent can be selected from the group comprising antimicrobials, anti aging, antivirals, anti-mycotics, anti-parasitics, anti-inflammatory, anthelminic drugs, anti hirsutism, anti wrinkle, pain management drugs, anti-worms, anti-ringworms, anti-warts, anti-yeast, erectile dysfunction drugs, vasodilators, vasoconstrictors, vitamins, colors, impetigo treatments, albinos treatment drugs, immuno suppressing agents, psoriasis drugs, melanin, pigments, peptides, amino-acids, hormones, anti cancer, analgesic, anesthetics, antihistamines, steroids, retinoids, seborrhea treatment drugs, acne drugs, atopic dermatitis drugs, rosacea drugs, vitiligo drugs, keratosis pilaris drugs treatment, alopecia drugs treatment, dermatitis drugs, eczema drugs, hyperhidrosis drugs, skin discoloration drugs, overactive bladder syndrome drugs, anti rheumatic pain drugs vaccines, antigens, sun screeners, as well as other drugs or combinations thereof In an embodiment of this invention, the at least one active agent is selected from antimicrobials, antivirals, anti-mycotics, anti-parasitics, anti-worms, anti-ringworms, anti-warts, anti-yeast, vasodilators, vasoconstrictors, vitamins, impetigo treatments, immuno suppressing agents, anti-psoriasis drugs, melanin, pigments, peptides, amino-acids, hormones, anti-cancer, analgesic, anesthetic, antihistamines, steroids, retinoids, anti-acne drugs, atopic dermatitis drugs, rosacea drugs, keratosis pilaris drugs, dermatitis drugs, anti-eczema drugs, anti-hyperhidrosis drugs, skin discoloration drugs and combinations thereof.

Exemplary agents can include, e.g., 5-fluorouracil, 19-nortestosterone, acetaminophen, acyclovir, alitretinoin, polypeptides, alprostadil, anti histamines, azatadine, azelaic acid, bacitracin, becaplermin, benzocaine, benzophenone, benzoyl peroxide, betamethasone, betamethasone dipropionate, betamethasone valerate, botox, botox like compounds, caffeine, capsaicin, ceramides, cetirizine, cimetidine, clindamycine, clobetasol propionate, clobetasone butyrate, clotrimazole, copper peptides, cortisone, corticosteroids, crotamiton, cyclizine, cyproheptadine, dexamethasone Na sulphate, diclofenac, diflucortolone valerate, dihydroxyacetone, diphenhydramine, docosanol, doxepin, eflornithine, erythromycin, estradiol, famotidine, famotidine, fatty acids, fexofenadine, flumethasone pivalate, glycyrrhizic acid, halobetasol, hormones, hydrocortisone, hydrocortisone 17-butyrate, hydroxyzine, ibuprofen, imiquimod, immunosuppressive agents, ivermectin, ketorolac, kojic acid, lidocaine, lindane, loratidine, mafenide acetate, masoprocol, melanin, melatonin, methylprednisolone aceponate, metronidazole, minoxidil, mometasone furoate, mupirocin, mycosinate, nabumetone, nadolol, neomycin, niacinamide, nicotine, octyl-methoxycinnamate, omega acids, oxybutynin, penciclovir, permethrin, peroxicam, phenothiazines, pimecrolimus, piperazine, piperonyl butoxide, podofliox, podophyllin, polymyxin, prilocalne, propylamine derivatives, prostaglandins, pyrethrins, ranitidine, retinoic acid, retinoid, RNA, DNA, salicylic acid, selenium sulfide, silver sulfadiazine, sodium sulfacetamide, steroids, sterols, sulfacetamide, sulfur, tacrolimus, terbinafine and/or one or more terbinafine salts, testosterone, tetracyclin, tizanidine tolterodine, triamcinolone acetonide, vancomycin, vitamins, vitamin A, vitamin D, vitamin D3 derivatives, vitamin E, whitening agents, other drugs and their salts or derivatives, and combinations thereof.

The nail or skin fungal infections can include, for example, onychomycosis, dermatomycosis, hyperkeratotic skin diseases, seborrheic eczema, thickened skin and chapped skin.

The antifungal agent can include ciclopirox, amorolfine, griseofulvine, posaconazole, itraconazole, econazole, butenafine, or other regulatory approved topical antifungal drug, as well as borax, geraniol (3,7-dimethylocta-2,6-dien-1-ol), terbinafine and/or one or more terbinafine salts or any combination of the foregoing.

In a further embodiment, the compositions of this invention comprise:
  a. 0.01-20% of at least one drug/active agent,
  b. 0.2-15% w/w of at least one film-forming ingredient,
  c. 0.2-20% w/w of at least one phospholipid,
  d. 50-90% w/w of at least one volatile solvent,
  e. 0-40% w/w water, preferably 15-40% water,
  f. 0-10% of an alkaline (basic) molecule,
  g. 0-30% of a hydrophilic agent such as glycols, trehalose, PCA, NaPCA,
  h. 0-10% of a base, selected from pharmaceutically acceptable bases, like but not limited to sodium hydroxide, potassium hydroxide, triethanolamine, tromethamine and ammonia.
  i. 0-5% of other pharmaceutically acceptable excipients, like but not limited to, plasticizers, emollients, sunscreens, pigments, antioxidants, stabilizers, perfumes, etc. according to need.

In a further embodiment, the compositions of this invention comprise:
  a. 0.01-20% of terbinafine and/or one or more of its salts.
  b. 0.2-15% w/w of at least one film-forming ingredient,
  c. 0.2-20% w/w of at least one phospholipid, d. 61-85% w/w of at least one volatile solvent.
e. 0-40% w/w water
f. 0-10% of an alkaline (basic) molecule
g. 0-30% of a hydrophilic agent such as glycols, trehalose, PCA, NaPCA,
h. 0-10% of a base, selected from pharmaceutically acceptable bases, like but not limited to sodium hydroxide, potassium hydroxide, triethanolamine, tromethamine and ammonia.
i. 0-5% of other pharmaceutically acceptable excipients, like but not limited to, plasticizers, emollients, sunscreens, pigments, antioxidants, stabilizers, perfumes, etc. according to need.

In yet another embodiment, the present invention provides a composition that includes about 10% w/w terbinafine hydrochloride, about 5% w/w of one or more phospholipids, about 0.2% w/w of Vitamin E, about 0.5% w/w Klucel, about 7% w/w of a 1N solution of sodium hydroxide, about 65% w/w ethanol, and water.

The phospholipid may be selected from, e.g., soy lecithin, egg lecithin, phosphatidylcholine, phosphatidylglycerol, phosphatidylinositol, phosphatidylserine, phosphatidylethanolamine, synthetic phospholipids, PEG-ylated phospholipids, phosphorylated lipids, phosphorylated vitamin E and mixtures thereof.

The concentration of the phospholipid in the compositions of the present invention preferably ranges from 0.2-20%.

The film-forming ingredient may be selected from, e.g., ethyl cellulose, esters of poly[methylvinyl ether/maleic acid] copolymer, PVP, PVA, PVP/PVA combinations, cationic cellulose polymers, chitosan, chitosan derivatives, polyacrylates, Eudragits, other pharmaceutically acceptable polymers or combinations thereof.

The film-forming ingredient in the compositions of the present invention can range from 0-15%, and preferably ranges from 0.5-5%, and more preferably from 0.5-2%.

In one embodiment the composition comprises a hydrophilic film-forming ingredient selected from cellulose derivatives, hydroxypropylcellulose, hydroxyethylcellulose, PVP and others.

In some embodiments, the film-forming ingredient includes a non-ionic, water-soluble cellulose ether such as, for example, hydroxypropylcellulose, an example of which includes Klucel®, e.g., Klucel® HF, a hydroxypropylcellulose that is sold in the United States by Hercules Inc., Wilmington, Del.

The volatile solvents preferably are selected from ethyl acetate, C2-C4 alcohols, ethanol, isopropanol, n-propanol and butanol (hereinafter "alcohol" or "alcohols"), and combinations thereof.

The glycol, which can be used in the compositions of the invention, is preferably selected from ethylene glycol, diethylene glycol, propylene glycol, dipropylene glycol, tetraglycol, butylene glycol, hexylene glycol and glycol esters or ethers like ethylene glycol monomethyl ether, diethylene glycol monoethyl ether, or other pharmaceutically acceptable glycols (hereinafter "glycol" or "glycols") and combinations thereof. Propylene glycol is among the preferred glycols. The glycol concentration (e.g., the propylene glycol concentration) is preferably from about 5 wt % to about 20 wt %, e.g., from about 5 wt % to about 15 wt % (e.g., about 13 wt %).

In another embodiment, the compositions comprise a phospholipid, ethanol, and water, a film forming ingredient, terbinafine or a terbinafine salt and optionally sodium hydroxide or potassium hydroxide.

In another preferred embodiment, the compositions comprise a phospholipid, ethanol, glycol, and water, terbinafine or a terbinafine salt, a film forming ingredient and optionally sodium hydroxide or potassium hydroxide.

In another preferred embodiment, the compositions comprise a phospholipid, ethanol, water, a hydrophilic film forming polymer, terbinafine or a terbinafine salt and optionally a base such as, e.g., sodium hydroxide or potassium hydroxide.

In another preferred embodiment, the compositions comprise a phospholipid, ethanol, and water, a hydrophilic film forming polymer, terbinafine, optionally glycol and optionally sodium hydroxide or potassium hydroxide.

In a preferred embodiment, the concentration of the active in the composition ranges from 0.01% to 20%.

In a preferred embodiment of this invention, there are provided nail and skin lacquers, providing a film containing phospholipid web-like structures over the treated nail and skin areas, thus improving the usefulness of the treatment.

In one preferred embodiment of the invention, the film structure is as exemplified in FIG. 1, FIG. 3, FIG. 5, FIG. 6, FIG. 7, FIG. 8, FIG. 9, FIG. 10, FIG. 11, FIG. 12, FIG. 13, FIG. 14, FIG. 15, FIG. 16 or FIG. 17.

The nail or skin fungal infections suitable for treatment in accordance with the present invention include, e.g., onychomycosis in its various forms.

The active in the instant compositions is terbinafine, in the form of a salt such as the hydrochloride, or the free base.

A preferred terbinafine topical solution comprises 10% terbinafine HCl, 5% phospholipid, 0.5-1.5% Klucel HF, 65% ethanol, 0-30% ethyl acetate, 7% sodium hydroxide solution (1N), and water to 100%

A preferred terbinafine topical solution comprises 10% terbinafine HCl, 5% phospholipid, 0.5-1.5% Klucel HF 65-75% ethanol 96, 0-30% ethyl acetate, 7% sodium hydroxide solution (1N), 0-13% propylene glycol and water to 100%.

The total concentration of all volatiles in the compositions can range from 61-95%, preferably from 61-90% or 65-90%, and more preferably from 70-85%.

Another preferred terbinafine topical solution comprises 10% terbinafine HCl, 5% phospholipid, 0.5-1.5% Klucel HF, 63% ethanol, 0-30% ethyl acetate, potassium hydroxide solution (1N), and water to 100%.

Another preferred terbinafine topical solution does not contain water as an added ingredient and comprises 10% terbinafine HCl, 5% phospholipid, 0.7% Klucel HF and ethanol to 100% or a combination of ethanol and ethyl acetate to 100%.

A total high concentration of all the volatiles in the compositions is desirable, being conducive to a rapid drying time and film formation.

The concentration of volatiles in the composition can range, e.g., from 50-95%, more preferably from 50% to 85%. Yet more preferably concentration of volatiles in the composition ranges from 60-90%, and more preferably from 65-850.

In another embodiment, the compositions comprise a phospholipid, ethanol, and water, a film forming ingredient, at least one active and optionally sodium hydroxide or potassium hydroxide.

In yet another embodiment, the composition of the invention comprises a phospholipid, ethanol, glycol, and water, a film forming ingredient, an active agent, optionally sodium hydroxide or potassium hydroxide.

In still another embodiment, the composition of the invention comprises a phospholipid, ethanol, water, a hydrophilic film forming polymer, at least one active and optionally a base like sodium hydroxide or potassium hydroxide.

In still yet another embodiment, the composition of the invention comprises a phospholipid, ethanol, and water, a hydrophilic film forming polymer, an active agent, optionally glycol and optionally sodium hydroxide or potassium hydroxide.

The concentration of the active agent in the composition of the invention can range from 0.01% to 20%.

In some embodiments, the present invention provides nail and skin lacquers, providing a film containing phospholipid web-like structures over the treated nail and skin areas, thus improving the usefulness of the treatment.

In other embodiments, the present invention provides compositions that form an occlusive structured film over skin and mucosal areas afflicted by various skin afflictions, thus improving the treatment of said skin afflictions. The skin afflictions suitable for treatment by said method of treatment are selected from psoriasis, eczema, acne, fungal infections, atopic dermatitis, immune system diseases, antimicrobial infections, viral infections, warts, impetigo, skin discoloration, cancer, dermatitis, inflammation, hyperhidrosis, alopecia, onychomycosis, rosacea, pain, allergy or varicose veins.

The nail or skin fungal infections suitable for treatment include, e.g., onychomycosis, dermatomycosis, hyperkeratotic skin diseases, seborrheic eczema, viral infections, impetigo, inflammation, warts, thickened skin and chapped skin.

In one embodiment, the preferred active agent in the instant compositions is terbinafine and/or one or more of its salts.

In another embodiment, the preferred active agent in the instant compositions is lidocaine, or Lidocaine HCl.

A preferred lidocaine topical composition comprises 5% lidocaine, 2% phospholipid, 0.5-1.5% Klucel® HF, 65% ethanol 96, 0-30% ethyl acetate, 0-10% propylene glycol, and water to 100%

Another preferred lidocaine topical composition comprises 7% lidocaine HCl, 3-6% phospholipid, 0.3-1.5% Klucel® HF, 60-85% ethanol, 0.3% vitamin E, 0-20% propylene glycol and water to 100%

A preferred tizanidine HCL topical composition comprises 5% tizanidine HCl, 4% phospholipid, 0.5-1.5% hydroxypropylethyl cellulose, 60-75% ethanol 96, 0-13% Isopropyl alcohol and water to 100%.

The concentration of ciclopirox in the compositions of this invention preferably ranges from 0.1% to 20% and more preferably 1% to 15%.

The concentration of griseofulvine in the compositions of this invention preferably ranges from 0.1% to 20% and more preferably 1% to 15%.

The concentration of amorolfine in the compositions of this invention preferably ranges from 0.1% to 20% and more preferably 1% to 15%.

The concentration of posaconazole in the compositions of this invention preferably ranges from 0.1% to 20% and more preferably 1% to 15%.

The nail and skin afflictions treated by the compositions of this invention are caused by dermatophytes, non-dermatophytic molds, yeast, fungi, yeasts, moulds or bacteria, including microorganisms selected from *Candida, Trychophyton rubrum, Trichophyton interdigitale, Epidermophyton floccosum, Trichophyton violaceum, Microsporum gypseum, Trichophyton tonsurans, Trichophyton soudanense, Trichophyton verrucosum, Neoscytalidium, Scopulariopsis, Aspergillus*, or a combination thereof.

In an additional embodiment of this invention, there are provided methods of treatment of nail and skin fungal infections by topical administration of the compositions of the present invention to the afflicted area of nail or skin as a solution, lotion, gel, foam, cream, spray or spray lacquer, whereby after the application a film is formed on the nail or skin exhibiting phospholipid-polymer structures, generating a drug reservoir in the film. More specifically, the method of treating a nail or skin fungal infection in a human in need thereof, comprising applying to the nail or skin a therapeutically effective dose of the composition of the invention and allowing the composition to dry, thereby forming a film. Another preferred embodiment is a method of treating nail or skin afflictions, the method comprising contacting the afflicted nail or skin the the composition of the present invention, thereby forming an occlusive film over the nail or skin.

In a preferred embodiment of this invention, the compositions are topical solutions, to be applied evenly on the skin or nail with a brush, spatula, pipette, applicator, metered spray or mist, sponge or patch. The compositions are preferably in the form of a topical solution or spray, whereby the solution or spray is capable of being applied to a nail or skin surface with a brush or a metered dose device, thereby forming a film when allowed to dry. The invention further relates to a dispensing device with the composition of the present invention contained therein.

The volatiles in the composition evaporate rapidly after application, leaving on the nail a thin cohesive film substantive to the applied surface containing phospholipid structured reservoirs that release the drug(s) to the site of application.

The application may be done once to multiple times daily and repeated as per physician's instructions. The composition should be applied evenly over the entire nail plate and 5 mm of surrounding skin. If possible, it should be applied to the nail bed, and the under surface of the nail plate when it is free of the nail bed. The next day, an additional application is done on the previous coat or on the cleaned nail plate.

Removal of the unattached, infected nail, as frequently as monthly, by a healthcare professional may be needed. The effectiveness of said compositions could enable a shortened period of treatment with superior results.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

EXAMPLES

The following examples further illustrate the invention but, of course, should not be construed as in any way limiting its scope.

Example 1

The compositions of Formulation No. I and comparison Formulation No. II are detailed in Table No. 1 below:

TABLE NO. 1

| Ingredients | Formulation No. I % w/w | Formulation No. II (phospholipid-free for comparison only) % w/w |
| --- | --- | --- |
| Ethanol (96%) | 65.36 | 69.93 |
| Phospholipid | 6.54 | — |
| Hydroxy propylcellulose | 1.96 | 2.1 |
| Water | To 100 | To 100 |

Figure 2:
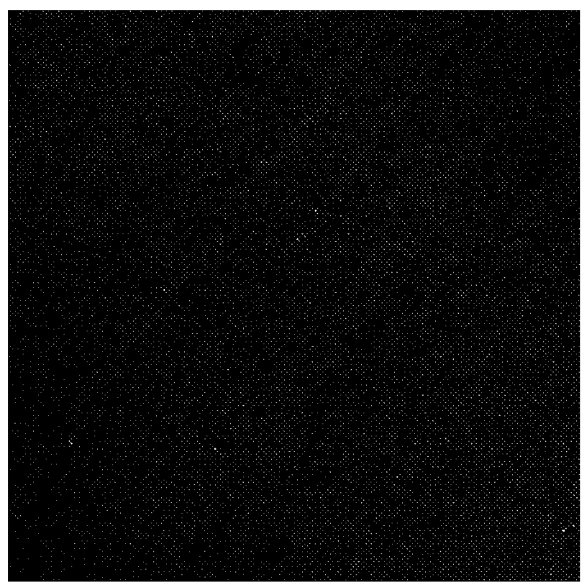
FIG. 2 depicts a fluorescence micrograph image of the film obtained from Formulation No. II—Olympus Fluoview 1XLO Confocal Laser Scanning Microscope. The probe used Fluorescein DHPE (N-(fluorescein-5-thiocarbamoyl)-1,2-dihexadecanoyl-sn-glycero-3-phosphoethanolamine triethylammonium salt) Invitrogen™. This formulation does contain polymer, but lacks phospholipid. No structures are evident, and only weak spots of fluorescence could be observed due to absence of the web-like film structure.
Figure 3:
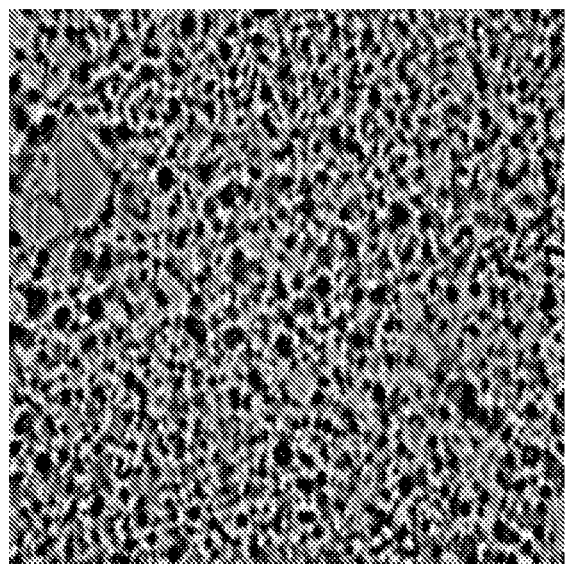
FIG. 3 depicts a light micrograph image of the film obtained from Formulation No. I—Axioscope Zeiss microscope, connected by a C-mount to a video camera, a TV screen and a PC. The phospholipid-polymer webbed structures are evident here.
Figure 4:
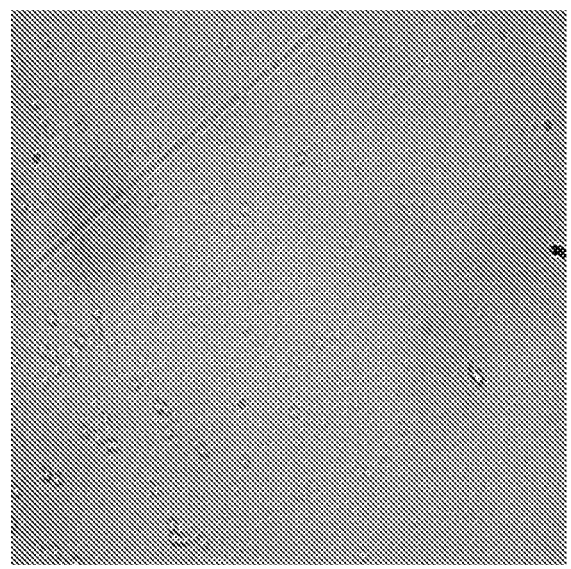
FIG. 4 depicts a light micrograph image of the film formed by Formulation No. II—Axioscope Zeiss light microscope, connected by a C-mount to a video camera, a TV screen and a PC. The formulation contains polymer but not phospholipid. The formulation contains polymer but not phospholipid. No web-like structures are present in the film.

Comparison between Formulation No. I (Fluorescence Microscopy FIG. 1 and light microscopy FIG. 3) which comprises phospholipid and hydroxypropylcellulose (Klucel HF) and Formulation No. II (Fluorescence Microscopy FIG. 2 and light microscopy FIG. 4) that did not contain phospholipid. It can be seen that only Formulation No. I, containing phospholipid, produced a film containing web-like structures, while Formulation No. II, lacking phospholipid, did not.

Formulation No. I—Method of Preparation

In a closed vessel, the phospholipid was dissolved in ethanol. Water was added to the above solution while mixing at 700 RPM with a Heidolph RZR-2000 Mechanical Overhead Stirrer equipped with "in house made" Pitched Propeller Blade Impeller from stainless steel (6 cm diameter).

Hydroxypropyl cellulose was dispersed speedily to the above composition with continuous mixing at 700 RPM by Heildolph RZR-2000 Stirrer equipped with Pitched Propeller Blade. The composition was left to rest for 12 hours.

The composition was mixed thoroughly at 700 RPM by Heildolph RZR-2000 Stirrer equipped with Pitched Propeller Blade.

The solution obtained applied to the nail or skin produces a film adherent to the applied area.

A drop of the above formulations was applied and spread on a slide glass and left at room temperature to allow evaporation of the solvents and film formation. The slides were observed by light microscopy and CLSM.

Light microscope imaging was assessed using an Axioscope Zeiss microscope, connected by a C-mount to a video camera, a TV screen and a PC.

Fluorescence imagining was performed by means of Olympus Fluoview 1XLO Confocal Laser Scanning Microscope with the probe Fluorescein DHPE (N-(fluorescein-5-thiocarbamoyl)-1,2-dihexadecanoyl-sn-glycero-3-phosphoethanolamine, triethylammonium salt) Invitrogen™.

Example 2

TABLE NO. 2

| Ingredients | Formulation No. III % w/w |
| --- | --- |
| Ethanol (96%) | 65 |
| Lidocaine | 5 |
| Phospholipid | 2 |
| Propylene Glycol | 10 |
| Vitamin E | 0.2 |
| Hydroxy propylcellulose | 0.6 |
| Water | To 100 |

Preparation Method of Formulation No. III

In a closed vessel, phospholipid, lidocaine and vitamin E were dissolved in ethanol-propylene glycol mixture with continuous mixing at 700 RPM. Water was added with continuous mixing. Hydroxypropylcellulose was dispersed to the above composition with continuous mixing at 700 RPM for 15 minutes. The composition left rest for about until next day and then mixed again for ten minutes. A clear homogenic formulation was obtained.

Figure 5:
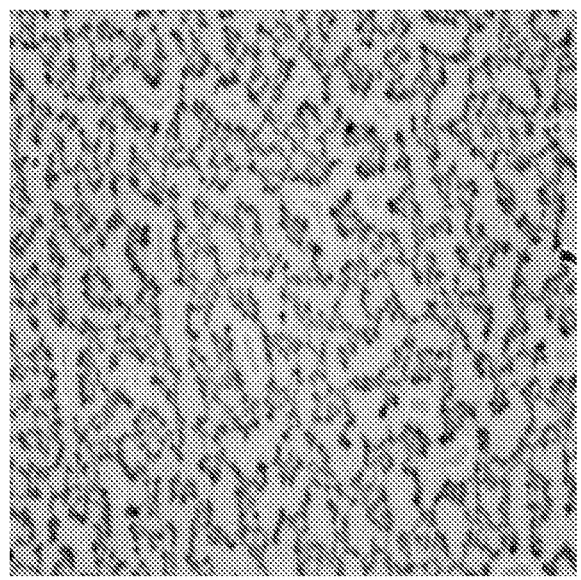
FIG. 5 depicts a light micrograph image of the film obtained from Formulation No. III—Axioscope Zeiss microscope, connected by a C-mount to a video camera, a TV screen and a PC. The formulation contains lidocaine phospholipid and polymer. The web-like structure clearly appears in the figure.

A drop of the above formulation was applied and spread on a slide glass and left at room temperature for to allow evaporation of the solvents and film formation. The slides were observed by light microscopy. Light microscope imaging was assessed using an Axioscope Zeiss microscope, connected by a C-mount to a video camera, a TV screen and a PC. A film containing web-like structures is observed (FIG. 5).

Example 3

TABLE NO. 3

| Ingredients | Formulation No. IV % w/w | Formulation No. V % w/w |
| --- | --- | --- |
| Lidocaine HCl | 7 | 10 |
| Phospholipid | 3 | 5 |
| Hydroxypropyl cellulose | 0.3 | 0.3 |
| Propylene glycol | 7 | 10 |
| Vitamin E | 0.3 | 0.4 |
| Ethanol (96%) | 60 | 68 |
| Water | To 100 | To 100 |

Preparation Method of Formulations No. IV and No. V

In a closed vessel, phospholipid and vitamin E were dissolved in ethanol-propylene glycol mixture with continuous mixing at 700 RPM. Lidocaine HCl was dissolved in water and the aqueous solution was added with continuous mixing to the above solvents mixture. Hydroxypropylcellulose was dispersed to the above composition with continuous mixing at 700 RPM for 15 minutes. The composition was left to rest until next day and then mixed again for ten minutes. A clear homogeneous formulation was obtained.

Example 4

TABLE NO. 4

| Ingredients | Formulation No. VI % w/w |
| --- | --- |
| Amorolfine | 5 |
| Phospholipid | 3 |
| Hydroxypropyl cellulose | 0.6 |
| Propylene glycol | 10 |
| Vitamin E | 0.2 |
| Ethanol (96%) | 70 |
| Water | To 100 |

Example 5

TABLE NO. 5

| Ingredients | Formulation No. VII % w/w |
| --- | --- |
| Ciclopirox olamine | 8 |
| Phospholipid | 5 |

TABLE NO. 5-continued

| Ingredients | Formulation No. VII % w/w |
|---|---|
| Hydroxypropyl cellulose | 0.6 |
| Vitamin E | 0.2 |
| Ethanol (96%) | 74 |
| Water | To 100 |

Example 6

TABLE NO. 6

| Ingredients | Formulation No. VIII % w/w |
|---|---|
| cimetidine | 2 |
| Phospholipid | 4.5 |
| Hydroxypropyl cellulose | 0.25 |
| Vitamin E | 0.4 |
| Ethanol (96%) | 80 |
| Water | To 100 |

Example 7

TABLE NO. 7

| Ingredients | Formulation No. XIII % w/w |
|---|---|
| 5FU | 5 |
| Phospholipid | 1 |
| Hydroxypropyl cellulose | 1 |
| Vitamin E | 0.4 |
| Ethanol (96%) | 60 |
| Propylene glycol | 10 |
| Water | To 100 |

Example 8

TABLE NO. 8

| Ingredients | Formulation No. IX % w/w |
|---|---|
| Betamethasone | 0.1 |
| Phospholipid | 2.5 |
| Hydroxypropyl cellulose | 0.7 |
| Vitamin E | 0.2 |
| Ethanol (96%) | 60 |
| Propylene glycol | 15 |
| Water | To 100 |

Example 9

TABLE NO. 9

| Ingredients | Formulation No. X % w/w |
|---|---|
| Clotrimazole | 1 |
| Dexamethasone acetate | 0.044 |

TABLE NO. 9-continued

| Ingredients | Formulation No. X % w/w |
|---|---|
| Neomycin | 0.645 |
| Vitamin E | 0.2 |
| Phospholipid | 3 |
| Hydroxypropyl cellulose | 0.6 |
| Vitamin E | 0.3 |
| Ethanol (96%) | 62 |
| Propylene glycol | 8 |
| Water | To 100 |

Example 10

TABLE NO. 10

| Ingredients | Formulation No. XI % w/w |
|---|---|
| Testosterone | 1 |
| Vitamin E | 0.2 |
| Phospholipid | 3 |
| Vitamin E | 0.3 |
| Isopropyl myristate | 4 |
| Ethanol (96%) | 62 |
| Carbopol 980 | 2 |
| Sodium hydroxide | q.s to nutralize the gel |
| Water | To 100 |

Example 11

TABLE NO. 11

| Ingredients | Formulation No. XII % w/w |
|---|---|
| Finasteride | 1 |
| Vitamin E | 0.2 |
| Phospholipid | 2.5 |
| Hydroxypropyl cellulose | 0.4 |
| Propylene glycol | 16 |
| Ethanol (96%) | To 100 |

Example 12

TABLE NO. 12

| Ingredients | Formulation No. XIII % w/w |
|---|---|
| Tizanidine HCL | 5 |
| Polyol | 5 |
| Phospholipid | 4 |
| Hydroxypropylethyl cellulose | 0.4 |
| Isopropyl alcohol | 10 |
| Ethanol (96%) | 60 |
| Water | To 100 |

Example 13

TABLE NO. 13

| Ingredients | Formulation No. XIV<br>% w/w |
|---|---|
| Niacinamide | 3.93 |
| Ethanol | 68.94 |
| Phospholipon 90G | 3.32 |
| Klucel HF | 0.99 |
| Propylene glycol | 8.96 |
| Water | To 100 |

Figure 6:
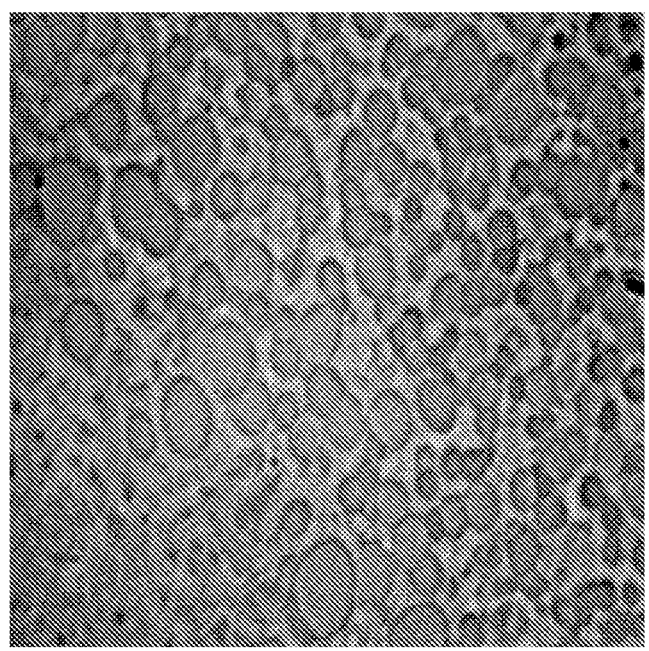
FIG. 6 depicts a light micrograph image of the film obtained from Formulation No. XIV—Axioscope Zeiss microscope, connected by a C-mount to a video camera, a TV screen and a PC. The formulation contains niacinamide phospholipid and polymer. The web-like structure clearly appears in the figure.

Formulation No. XIV was prepared according to the methods described above. A drop of the above formulation was applied and spread on a slide glass and left at room temperature to allow evaporation of the solvents and film formation. The slides were observed by light microscopy. Light microscope imaging was assessed using an Axioscope Zeiss microscope, connected by a C-mount to a video camera, a TV screen and a PC. A film containing web-like structures was observed (FIG. 6).

Example 14

TABLE NO. 14

| Ingredients | Formulation No. XV<br>% w/w |
|---|---|
| Bacitracin | 0.351 |
| Ethanol | 64.24 |
| Phospholipon 90G | 6.42 |
| Klucel HF | 1.92 |
| Propylene glycol | 17.35 |
| Water | To 100 |

Figure 7:
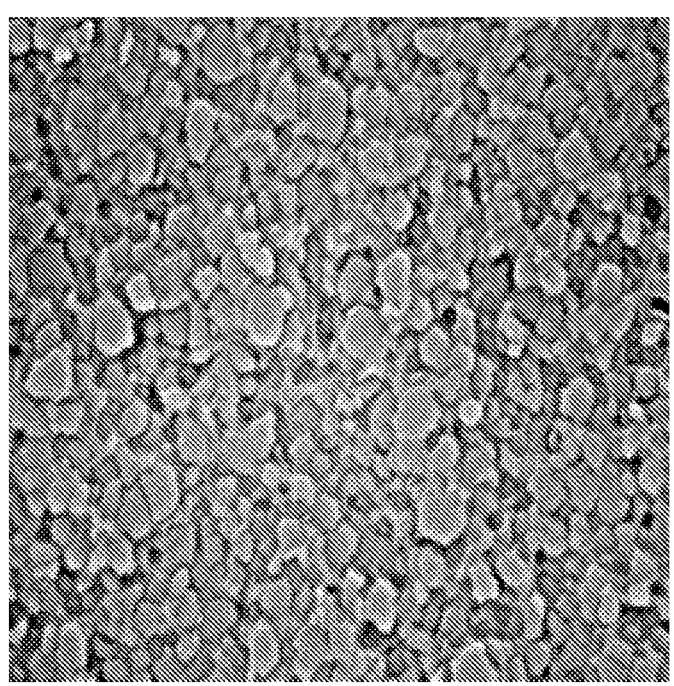
FIG. 7 depicts a light micrograph image of the film obtained from Formulation No. XV—Axioscope Zeiss microscope, connected by a C-mount to a video camera, a TV screen and a PC. The formulation contains bacitracin phospholipid and polymer. The web-like structure clearly appears in the figure.

Formulation No. XV was prepared according to the methods described above. A drop of the above formulation was applied and spread on a slide glass and left at room temperature to allow evaporation of the solvents and film formation. The slides were observed by light microscopy. Light microscope imaging was assessed using an Axioscope Zeiss microscope, connected by a C-mount to a video camera, a TV screen and a PC. A film containing web-like structures was observed (FIG. 7).

Example 15

TABLE NO. 15

| Ingredients | Formulation No. XVI<br>% w/w |
|---|---|
| Octyl-methoxycinnamate | 4.08 |
| Ethanol | 62.22 |
| Phospholipon 90G | 3.68 |
| Klucel HF | 0.29 |
| Water | To 100 |

Figure 8:
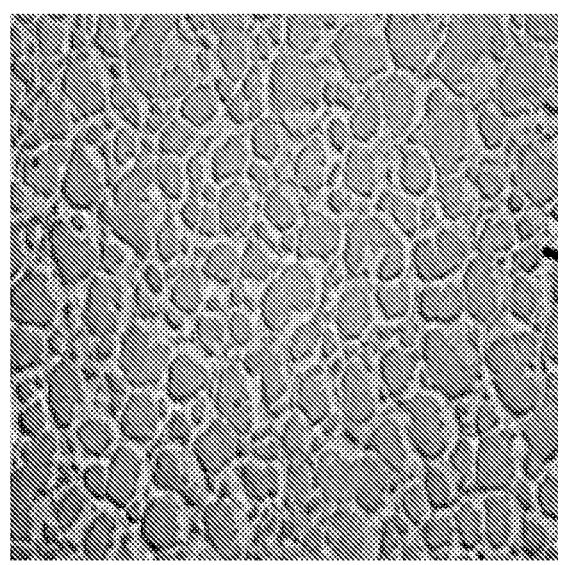
FIG. 8 depicts a light micrograph image of the film obtained from Formulation No. XVI—Axioscope Zeiss microscope, connected by a C-mount to a video camera, a TV screen and a PC. The formulation contains octylmethoxycinnamate, phospholipid and polymer. The web-like structure clearly appears in the figure.

Formulation No. XVI was prepared according to the methods described above. A drop of the above formulation was applied and spread on a slide glass and left at room temperature to allow evaporation of the solvents and film formation. The slides were observed by light microscopy. Light microscope imaging was assessed using an Axioscope Zeiss microscope, connected by a C-mount to a video camera, a TV screen and a PC. A film containing web-like structures was observed (FIG. 8).

Example 16

TABLE NO. 16

| Ingredients | Formulation No. XVII<br>% w/w |
|---|---|
| Ciclopirox olamine | 8.14 |
| Ethanol | 63.21 |
| Phospholipon 90G | 3.57 |
| Klucel HF | 0.28 |
| Water | To 100 |

Figure 9:
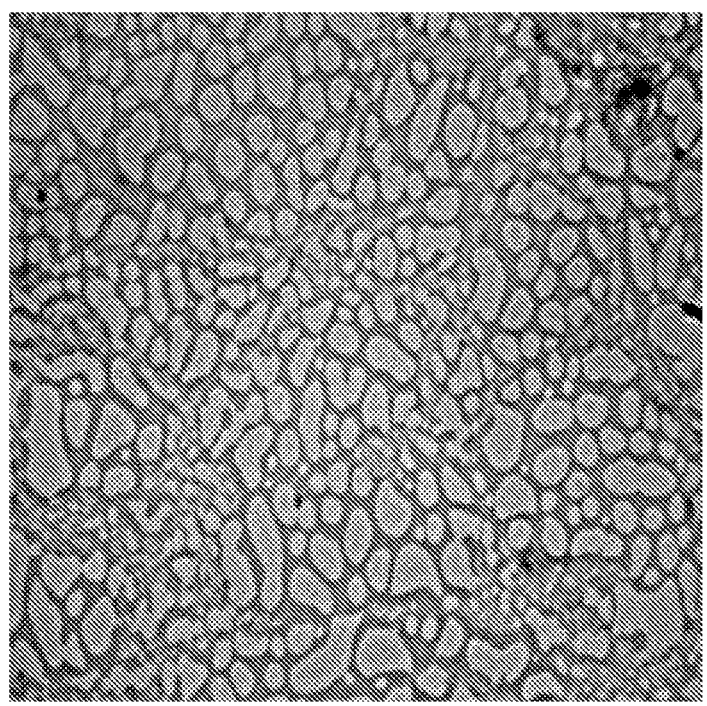
FIG. 9 depicts a light micrograph image of the film obtained from Formulation No. XVII—Axioscope Zeiss microscope, connected by a C-mount to a video camera, a TV screen and a PC. The formulation contains ciclopirox olamine, phospholipid and polymer. The web-like structure clearly appears in the figure.

Formulation No. XVII was prepared according to the methods described above. A drop of the above formulation was applied and spread on a slide glass and left at room temperature to allow evaporation of the solvents and film formation. The slides were observed by light microscopy. Light microscope imaging was assessed using an Axioscope Zeiss microscope, connected by a C-mount to a video camera, a TV screen and a PC. A film containing web-like structures was observed (FIG. 9).

Example 17

TABLE NO. 17

| Ingredients | Formulation No. XVIII<br>% w/w |
|---|---|
| Clotrimazole | 1 |
| Ethanol | 63 |
| Phospholipon 90G | 6.7 |
| Klucel HF | 2 |
| Water | To 100 |

Figure 10:
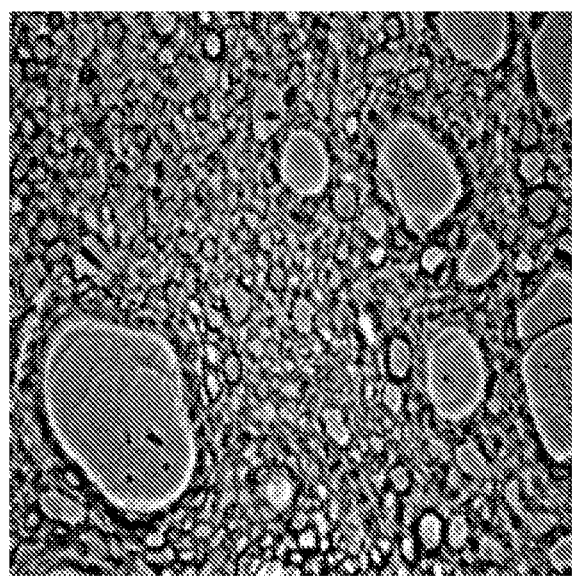
FIG. 10 depicts a light micrograph image of the film obtained from Formulation No. XVIII—Axioscope Zeiss microscope, connected by a C-mount to a video camera, a TV screen and a PC. The formulation contains clotrimazole, phospholipid and polymer. The web-like structure clearly appears in the figure.

Formulation No XVIII was prepared according to the methods described above. A drop of the above formulation was applied and spread on a slide glass and left at room temperature to allow evaporation of the solvents and film formation. The slides were observed by light microscopy. Light microscope imaging was assessed using an Axioscope Zeiss microscope, connected by a C-mount to a video camera, a TV screen and a PC. A film containing web-like structures was observed (FIG. 10).

Example 18

TABLE NO. 18

| Ingredients | Formulation No. XIX<br>% w/w |
|---|---|
| Estradiol | 1 |
| Ethanol | 67.5 |
| Phospholipon 90G | 4.5 |
| Klucel HF | 0.36 |
| Water | To 100 |

Formulation No. XIX was prepared according to the methods described above. A drop of the above formulation was applied and spread on a slide glass and left at room temperature to allow evaporation of the solvents and film formation. The slides were observed by light microscopy.

Figure 11:
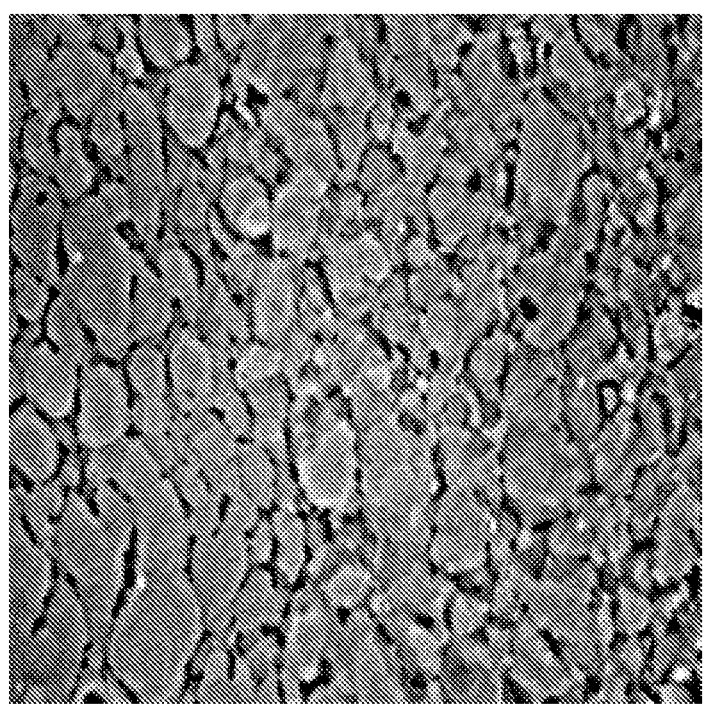
FIG. 11 depicts a light micrograph image of the film obtained from Formulation No. XIX—Axioscope Zeiss microscope, connected by a C-mount to a video camera, a TV screen and a PC. The formulation contains estradiol, phospholipid and polymer. The web-like structure clearly appears in the figure.
Figure 12:
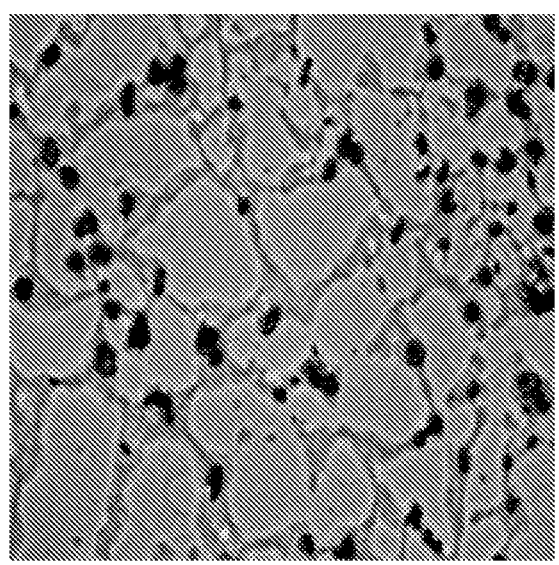
FIG. 12 depicts a light micrograph image of the film obtained from Formulation No. XX—Axioscope Zeiss microscope, connected by a C-mount to a video camera, a TV screen and a PC. The formulation contains flumethasone pivalate 3%, phospholipid and polymer. The web-like structure clearly appears in the figure.

Light microscope imaging was assessed using an Axioscope Zeiss microscope, connected by a C-mount to a video camera, a TV screen and a PC. A film containing web-like structures was observed (FIG. 11).

Example 19

TABLE NO. 19

| Ingredients | Formulation No. XX % w/w | Formulation No. XXI % w/w |
|---|---|---|
| Flumethasone pivalate | 3 | 0.28 |
| Ethanol | 65.5 | 67.46 |
| Phospholipon 90G | 4.5 | 4.45 |
| Klucel HF | 0.36 | 0.35 |
| Water | To 100 | To 100 |

Figure 13:
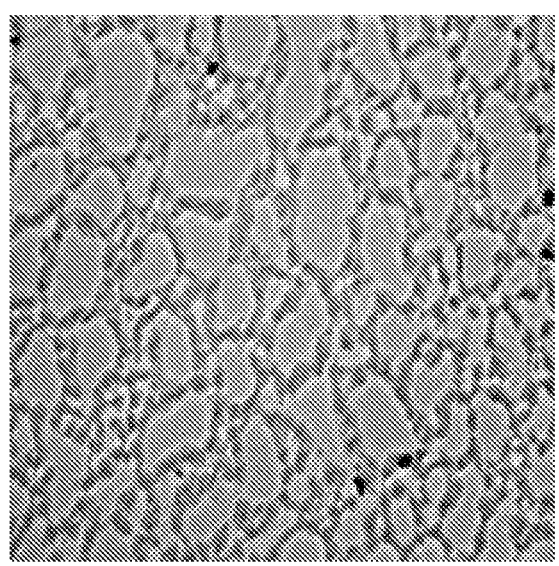
FIG. 13 depicts a light micrograph image of the film obtained from Formulation No. XXI—Axioscope Zeiss microscope, connected by a C-mount to a video camera, a TV screen and a PC. The formulation contains flumethasone pivalate 0.28%, phospholipid and polymer. The web-like structure clearly appears in the figure.

Formulations Nos. XX and XXI were prepared according to the methods described above. A drop of the above formulations was applied and spread on a slide glass and left at room temperature to allow evaporation of the solvents and film formation. The slides were observed by light microscopy. Light microscope imaging was assessed using an Axioscope Zeiss microscope, connected by a C-mount to a video camera, a TV screen and a PC. A film containing web-like structures was observed for Formulation XX (FIG. 12) and Formulation XXI (FIG. 13).

Example 20

TABLE NO. 20

| Ingredients | Formulation No. XXII % w/w |
|---|---|
| Ibuprofen | 4.16 |
| Ethanol | 65.22 |
| Phospholipon 90G | 3.67 |
| Klucel HF | 0.29 |
| Water | To 100 |

Figure 14:
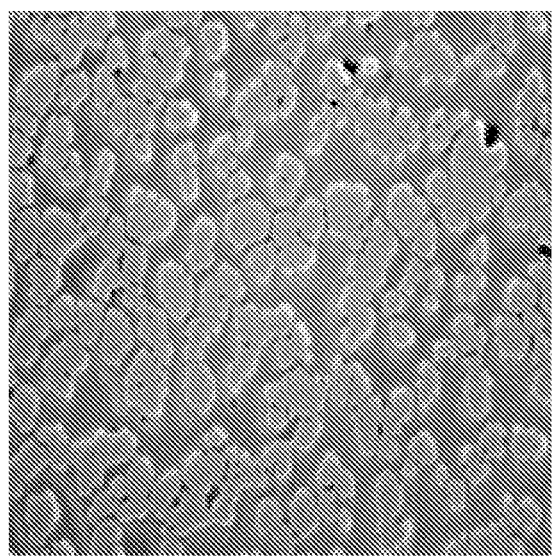
FIG. 14 depicts a light micrograph image of the film obtained from Formulation No. XXII—Axioscope Zeiss microscope, connected by a C-mount to a video camera, a TV screen and a PC. The formulation contains ibuprofen, phospholipid and polymer. The web-like structure clearly appears in the figure.
Figure 15:
FIG. 15 depicts a light micrograph image of the film obtained from Formulation No. XXIII—Axioscope Zeiss microscope, connected by a C-mount to a video camera, a TV screen and a PC. The formulation contains no water, phospholipid and polymer. The web-like structure clearly appears in the figure.
Figure 16:
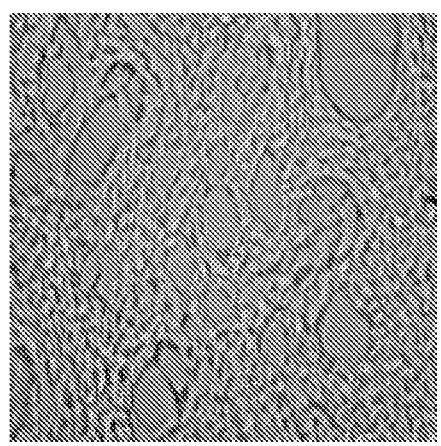
FIG. 16 depicts a light micrograph image of the film obtained from Formulation No. XXIV—Axioscope Zeiss microscope, connected by a C-mount to a video camera, a TV screen and a PC. The formulation contains no water, phospholipid and polymer. The web-like structure clearly appears in the figure.

Formulation No XXII was prepared according to the methods described above. A drop of the above formulation was applied and spread on a slide glass and left at room temperature to allow evaporation of the solvents and film formation. The slides were observed by light microscopy. Light microscope imaging was assessed using an Axioscope Zeiss microscope, connected by a C-mount to a video camera, a TV screen and a PC. A film containing web-like structures was observed (FIG. 14).

Example 21

TABLE NO. 21

Water-free formulations

| Ingredients | Formulation No. XXIII % w/w | Formulation No. XXIV % w/w |
|---|---|---|
| Ethanol (96%) | 71.43 | 88.50 |
| Phospholipid | 7.14 | 8.85 |
| Klucel | 2.14 | 2.65 |
| Propylene glycol | 7.14 | — |

Preparation Method of Formulations No. XXII and XXIV

In a closed vessel, phospholipid was dissolved in ethanol and propylene glycol if present with continuous mixing at 700 RPM by Heildolph RZR-2000 stirrer equipped with Pitched Propeller Blade. Klucel was dispersed speedily to the above composition with continuous mixing at 700 RPM. The composition was left to rest for about 12 hours, then mixed thoroughly.

A drop of the above formulations was applied and spread on a slide glass and left at room temperature for to allow evaporation of the solvents and film formation. The slides were observed by light microscopy. Light microscope imaging was assessed using an Axioscope Zeiss microscope, connected by a C-mount to a video camera, a TV screen and a PC. A film containing web-like structures was observed (FIG. 15 for formulation XXIII and FIG. 16 for Formulation XXIV).

Example 22

The composition of Formulation No. T-I is detailed in Table No. 22 below:

TABLE NO. 22

Water-free formulation

| Ingredients | Formulation No. T-I % w/w |
|---|---|
| Terbinafine HCL | 12 |
| Phospholipid | 7.14 |
| Vitamin E | 0.2 |
| Hydroxy propylcellulose | 2.14 |
| Ethanol (96%) | to 100 |

Preparation Method of Formulation No. T-I

In a closed vessel, dissolve phospholipid, terbinafine HCl and vitamin E in ethanol with continuous mixing at 700 RPM by Heildolph RZR-2000 stirrer equipped with Pitched Propeller Blade. Disperse hydroxypropylcellulose speedily to the above composition with continuous mixing at 700 RPM. Leave the composition to rest for about 12 hours. Then mix the composition thoroughly.

Example 23

The composition of Formulation No. T-II is detailed in Table No. 23 below:

TABLE NO. 23

| Ingredients | Formulation No. T-II % w/w |
|---|---|
| Terbinafine HCL | 10 |
| Phospholipid | 5 |
| Vitamin E | 0.2 |
| Klucel | 0.5 |
| NaOH 1N sol. | 7 |
| Ethanol | 65 |
| Water | To 100 |

Method of Preparation of Formulation No. T-II

The phospholipid was dissolved in ethanol, and vitamin E was added thereto. Terbinafine HCl was dissolved in the above ethanolic solution. The solution was mixed with a mechanical mixer until the drug was dissolved. Sodium hydroxide solution was added with continuous mixing. Klucel was dispersed speedily on the surface of the above composition with continuous mixing. The composition was left for at least 12 hours for the dispersion of the polymer then mixed again until a homogenous liquid was obtained.

Figure 17:
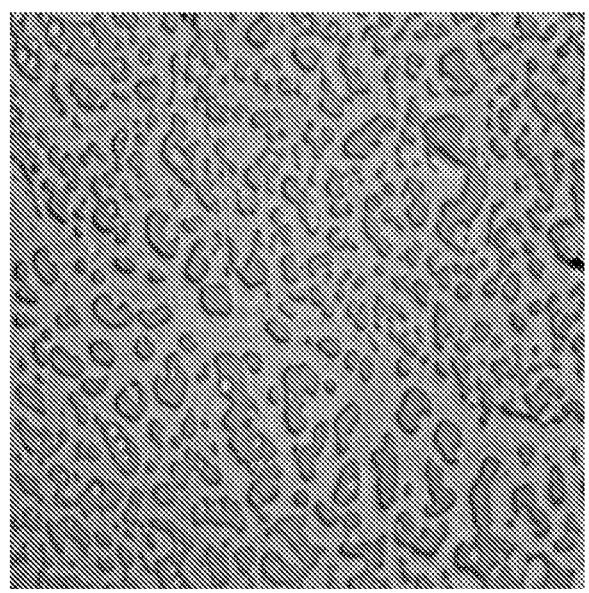
FIG. 17 depicts a light micrograph image of the film formed by Formulation No. T-II—Axioscope Zeiss microscope, connected by a C-mount to a video camera, a TV screen and a PC. The formulation contains terbinafine HCL and both phospholipid and polymer. The web-like structure clearly appears in the figure.

A drop from the above formulation was applied and spread on a slide glass and left at room temperature for 5 to 30 minutes to allow evaporation of the solvents and film formation. The slides were observed under a Zeiss light microscope connected by a C-mount to a video camera, a TV screen and a PC. The web-like structure is evident (FIG. 17)

Example 24

This example illustrates a protocol for evaluating the drug amount retained by the nail after application of a composition of the present invention on clipped nails.
Protocol of Experiment
1. Weigh 4 samples of about 10 mg nail pieces (clipped from a healthy adult male).
2. Place each nails sample on a microscope glass slide and add on the nails about 30 mg of each formulation tested.
3. Leave the slide uncovered for about 24 hours at Room Temperature.
4. By using tweezers, introduce the nail samples in an Eppendorf and wash the nails with 1.5 ml 50% ethanol by vortexing than remove and wash again in 1.5 ml distilled water by vortexing.
5. Remove the nail pieces, using tweezers, place them on filter paper and wipe with Kimwipes until they look dry.
6. Insert each sample to 0.5 ml safe-lock Eppendorf by using tweezers and add 0.5 ml ACN: MeOH: Water mixture.
7. Shake for 24 hours for extraction.
8. Withdraw the nails by using tweezers and centrifuge the extract at 5000 RPM for 15 min. Remove 400 µl of supernatant and place it in a 0.5 ml Eppendorf.
9. Filtrate through Acrodisk GHP 0.45µ into a safe-lock Eppendorf.
10. Inject samples to HPLC.

All references, including publications, patent applications, and patents, cited herein are hereby incorporated by reference to the same extent as if each reference were individually and specifically indicated to be incorporated by reference and were set forth in its entirety herein. In addition, the citation or identification of any reference in this application shall not be construed as an admission that such reference qualifies as prior art with respect to the present invention.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A topical film-forming composition comprising 0.01-20% of at least one active agent, 0.2-20% of a phospholipid, 60-85% of a volatile solvent selected from the group consisting of ethyl acetate, C2-C4 alcohols and combinations thereof, 0-40% water, 0-30% of a glycol, 0.2-15% of a film-forming ingredient, and 0-5% other pharmaceutically acceptable ingredients, whereby, following application of the composition onto the nail or skin, said volatile solvent evaporates, forming a film exhibiting a web-like structure.

2. The composition of claim 1, wherein said glycol is selected from the group consisting of ethylene glycol, diethylene glycol, propylene glycol, dipropylene glycol, tetraglycol, butylene glycol, hexylene glycol, glycol esters or ethers selected from the group consisting of ethylene glycol monomethyl ether and diethylene glycol monoethyl ether, other pharmaceutically acceptable glycols, and combinations thereof.

3. The composition of claim 1, wherein said at least one active agent is at least one active agent selected from the group consisting of antimicrobials, antivirals, anti-mycotics, anti-parasitics, anti-worm agents, anti-ringworm agents, anti-wart agents, anti-yeast agents, vasodilators, vasoconstrictors, vitamins, impetigo treatments, immuno suppressing agents, anti-psoriasis drugs, melanin, pigments, peptides, amino-acids, hormones, anti-cancer drugs, analgesics, anesthetics, antihistamines, steroids, retinoids, anti-acne drugs, atopic dermatitis drugs, rosacea drugs, keratosis pilaris drugs, dermatitis drugs, anti-eczema drugs, anti-hyperhidrosis drugs, and skin discoloration drugs.

4. The composition of claim 1, wherein said at least one active agent is at least one active agent selected from the group consisting of ciclopirox, amorolfine, griseofulvine, posaconazole, itraconazole, econazole, ibuprofen, butenafine, borax, geraniol, terbinafine, salts thereof.

5. A topical composition according to claim 1 for the treatment of nail or skin afflictions in a human or animal, wherein following the evaporation of volatiles, a continuous film is formed on the nail or skin surface treated, said film exhibiting a web-like structure comprising the active agent(s).

6. The composition of claim 5, wherein the nail or skin fungal infections are caused by dermatophytes, non-dermatophytic molds, yeast, fungi, moulds or bacteria, including microorganisms selected from *Candida, Trychophyton rubrum, Trichophyton interdigitale, Epidermophyton floccosum, Trichophyton violaceum, Microsporum gypseum, Trichophyton tonsurans, Trichophyton soudanense, Trichophyton verrucosum, Neoscytalidium, Scopulariopsis, Aspergillus*, or a combination thereof.

7. The composition of claim 1, wherein the phospholipid is selected from the group consisting of soy lecithin, egg lecithin, phosphatidylcholine, phosphatidylglycerol, phosphatidylinositol, phosphatidylserine, phosphatidylethanolamine, synthetic phospholipids, PEG-ylated phospholipids, phosphorylated lipids, phosphorylated vitamin E, and mixtures thereof.

8. The composition of claim 1, further including up to 5% of other pharmaceutically acceptable ingredients selected from the group consisting of glycols, trehalose, PCA, NaPCA, a base selected from the group consisting of pharmaceutically acceptable bases in the group consisting of sodium hydroxide, potassium hydroxide, triethanolamine and ammonia, borax, plasticizers, emollients, sunscreens, pigments, antioxidants, stabilizers, perfumes and combinations thereof.

9. The composition of claim 1, wherein said film-forming ingredient is a hydrophilic film-forming ingredient selected from the group consisting of cellulose derivatives, hydroxypropylcellulose, hydroxyethylcellulose, poly(vinyl pyrrolidone), and combinations thereof.

10. The composition of claim 1, wherein said film-forming ingredient is selected from the group consisting of ethyl cellulose, esters of poly(methylvinyl ether/maleic acid) copolymer, poly(vinyl acetate), poly(vinyl pyrrolidine), poly(vinyl acetate)/poly(vinyl pyrrolidine) combinations, cationic cellulose polymers, chitosan, chitosan derivatives, polyacrylates, Eudragits, and combinations thereof.

11. The composition of claim 1, in the form of a pharmaceutically acceptable form of administration, selected from a solution, a lotion, a gel, a foam, a cream, a spray and a spray lacquer.

12. The composition of claim 1, comprising the following components:
  0.01-20% of at least one antifungal drug selected from the group consisting of ciclopirox, amorolfine, griseofulvine, posaconazole, butenafine, itraconazole, terbinafine, and salts thereof,
  0.2-20% w/w of a lipid selected from the group consisting of phospholipids and phosphorylated lipids,
  60-85% of a volatile solvent selected from the group consisting of ethanol, isopropanol, n-propanol, butanol, ethyl acetate and combinations thereof,
  0-30% of a glycol selected from the group consisting of ethylene glycol, diethylene glycol, propylene glycol, dipropylene glycol, tetraglycol, butylene glycol, hexylene glycol and glycol esters or ethers, other pharmaceutically acceptable glycols, and combinations thereof,
  0.2-15% of a film-forming ingredient selected from the group consisting of cellulose derivatives, butyl monoester of poly(methylvinyl ether/maleic acid) copolymer, poly(vinyl acetate), poly(vinyl pyrrolidine), Eudragits, other pharmaceutically acceptable polymers, and combinations thereof,
  0-40% water,
  0-10% of a base selected from the group consisting of 0.5N to 1.0N aqueous solution of sodium hydroxide, potassium hydroxide, ammonia borax, and combinations thereof, and
  0-5% of other pharmaceutically acceptable excipients selected from the group consisting of plasticizers, emollients, sunscreens, pigments, antioxidants, stabilizers, perfumes, and combinations thereof.

13. The composition of claim 1, in the form of a topical solution or spray, whereby said solution or spray is capable of being applied to a nail or skin surface with a brush or a metered dose device, thereby forming a film when allowed to dry.

14. The composition of claim 1, wherein said at least one active agent is terbinafine or a pharmaceutically acceptable salt of terbinafine, said composition comprising 0.01-20% terbinafine or a pharmaceutically acceptable salt of terbinafine, 0.2-20% of a phospholipid, 61-85% of volatile solvents selected from the group consisting of C2-C4 alcohols and combinations thereof, 0-40% water, 0-30% of a glycol, 0.2-15% of a film-forming ingredient and 0-5% other pharmaceutically acceptable ingredients, whereby, upon application to a nail or skin surface and following the rapid evaporation of the volatiles, a continuous film is formed on the nail or skin surface treated, said film exhibiting a web-like structure comprising terbinafine or salt thereof.

15. The composition of claim 14, comprising 15-40% water.

16. The composition of claim 14, wherein the terbinafine is selected from the group consisting of terbinafine, terbinafine hydrochloride, and combinations thereof.

17. The composition of claim 14, comprising the following components:
  0.01-20% of terbinafine or one or more terbinafine salts,
  0.2-20% w/w of a lipid selected from the group consisting of phospholipids and phosphorylated lipids,
  61-85% of a volatile solvent selected from the group consisting of ethanol, isopropanol, n-propanol, butanol, ethyl acetate and combinations thereof,
  0-30% of a glycol selected from the group consisting of ethylene glycol, diethylene glycol, propylene glycol, dipropylene glycol, tetraglycol, butylene glycol, hexylene glycol and glycol esters or ethers, other pharmaceutically acceptable glycols, and combinations thereof,
  0.2-10% of a film-forming ingredient selected from the group consisting of cellulose derivatives, butyl monoester of poly(methylvinyl ether/maleic acid) copolymer, poly(vinyl acetate), poly(vinyl pyrrolidine), Eudragits, other pharmaceutically acceptable polymers, and combinations thereof,
  0-40% water,
  0-10% of 0.5N to 1.0N aqueous solution of a base selected from selected from the group consisting of sodium hydroxide, potassium hydroxide, ammonia borax, and combinations thereof, and 0-5% of other pharmaceutically acceptable excipients selected from the group consisting of plasticizers, emollients, sunscreens, pigments, antioxidants, stabilizers, perfumes, and combinations thereof.

18. The composition of claim 14, comprising about 10% w/w terbinafine hydrochloride, about 5% w/w of one or more phospholipids, about 0.2% w/w of Vitamin E, about 0.5% w/w hydroxypropylcellulose, about 7% w/w of a 1N solution of sodium hydroxide, about 65% w/w ethanol, and water.

19. The composition of claim 1, wherein the active agent is ibuprofen, said composition comprising 0.3-15% w/w ibuprofen.

20. A method of treating a nail or skin fungal infection in a human in need thereof, the method comprising applying to the nail or skin a therapeutically effective dose of the composition of claim 3, wherein the at least one active agent is an anti-mycotic, and allowing the composition to dry, thereby forming a film.

21. A method of treating nail or skin afflictions, the method comprising contacting the afflicted nail or skin with a therapeutically effective dose of the composition of claim 3, thereby forming an occlusive film over the nail or skin.

22. An article of manufacture comprising a dispensing device and the composition of claim 1 contained therein.

23. The composition according to claim 3 wherein said active agent is an analgesic.

24. A composition according to claim 23, wherein said analgesic is ibuprofen.

25. The composition of claim 5, wherein the nail or skin fungal afflictions are at least one affliction selected from the group consisting of onychomycosis, dermatomycosis, hyperkeratotic skin diseases, seborrheic eczema, viral infections, impetigo, inflammation, warts, thickened skin, and chapped skin.

26. A topical film-forming composition according to claim 1, wherein said volatile solvent is selected from the group consisting of ethanol, isopropanol, ethyl acetate and a mixture thereof.

27. A topical film-forming composition according to claim 26, wherein said volatile solvent is ethanol.

28. A topical film-forming composition according claim 1, comprising said glycol, wherein said glycol is propylene glycol.

29. A topical film-forming composition according claim 28, wherein said volatile solvent is ethanol.

30. A claim according to claim 1, wherein the concentration of the volatile solvent in the composition is from 65-85%.

\* \* \* \* \*